(12) United States Patent
Sayer et al.

(10) Patent No.: US 9,179,673 B2
(45) Date of Patent: *Nov. 10, 2015

(54) AUXIN HERBICIDE COMPOSITION

(71) Applicant: NUFARM AUSTRALIA LIMITED, Laverton North, Victoria (AU)

(72) Inventors: Chad Richard Ord Sayer, Brighton (AU); Graeme Sutton, Ashwood (AU); Aristos Panayi, Taylors Hill (AU)

(73) Assignee: NUFARM AUSTRALIA LIMITED, Laverton North, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 14/499,786

(22) Filed: Sep. 29, 2014

(65) Prior Publication Data
US 2015/0018212 A1 Jan. 15, 2015

Related U.S. Application Data

(63) Continuation of application No. 13/141,485, filed as application No. PCT/AU2009/000169 on Dec. 23, 2009, now Pat. No. 8,877,685.

(30) Foreign Application Priority Data

Dec. 23, 2008 (AU) .................... 2008906606

(51) Int. Cl.
*A01N 37/40* (2006.01)
*A01N 39/04* (2006.01)
*A01N 25/02* (2006.01)
*A01N 37/38* (2006.01)

(52) U.S. Cl.
CPC ............... *A01N 37/40* (2013.01); *A01N 37/38* (2013.01); *A01N 39/04* (2013.01)

(58) Field of Classification Search
CPC .............................. A01N 37/40; A01N 39/04
See application file for complete search history.

(56) References Cited

U.S. PATENT DOCUMENTS

| 8,871,683 | B2 * | 10/2014 | Sayer et al. | 504/324 |
| 8,877,685 | B2 * | 11/2014 | Sayer et al. | 504/323 |
| 2008/0032892 | A1 * | 2/2008 | Linton | 504/142 |

FOREIGN PATENT DOCUMENTS

GB 1339315 A * 12/1973

* cited by examiner

Primary Examiner — Sue Liu
Assistant Examiner — Nathan W Schlientz

(57) ABSTRACT

An aqueous liquid herbicide composition comprising a solution of at least one of 2,4-D and dicamba in the form of the monomethylamine salt and at least one of 2,4-D and dicamba in the form of the dimethylamine salt wherein the molar ratio of monomethylamine to dimethylamine is in the range of from 1:20 to 4:6.

9 Claims, 3 Drawing Sheets

AUXIN HERBICIDE COMPOSITION

FIELD

This invention relates to an auxin herbicide composition comprising at least one of 2,4-D and dicamba and in particular a composition of auxin herbicides in the form of salts which allows a high loading of active auxin herbicide comprising at least one of 2,4-D and dicamba to be provided in aqueous composition. The invention also relates to an aqueous composition of auxin herbicide salts having a high loading of at least one of 2,4-D and dicamba and the preparation of the salt composition and high loading aqueous composition and methods of controlling plant growth using the compositions.

BACKGROUND

Auxin herbicides have been widely used as herbicides and include phenoxyacids such as phenoxy-acetic, -propionic and -butyric acid herbicides and their esters; phenyl acid herbicides such as 3,6-dichloro-o-anisic acid; pyridyloxy acids such as 3,5,6,pyridyloxy acetic acid; and pyridine carboxylic acids such as 3,6-dichloropyridine-2-carboxylic acid. Phenoxy acetic acid herbicides including 2,4-Dichlorophenoxy acetic acid (2,4-D) and 4-chloro-2-methylphenoxy acetic acid (MCPA) and their esters such as the 2-ethylhexyl and butoxy ethanol esters are used to control broadleaf weeds in crops such as cereals, sugar cane turf pastures and the like. Auxin herbicides are generally of formula

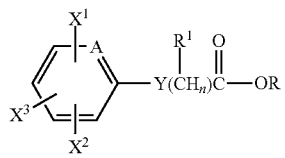

wherein
R is the alcohol portion of the ester or is a salt counter ion such a substituted ammonium counter ion;
A is nitrogen or CH;
$X^1$, $X^2$ and $X^3$ are independently selected from hydrogen, halogen (preferably chloro) and methyl, preferably from hydrogen and chloro and most preferably at least two of $X^1$, $X^2$ and $X^3$ are selected from chloro and methyl;
Y is a bond, oxgen or 1,4-oxyphenoxy;
$R^1$ is selected from hydrogen and methyl and preferably is hydrogen; and
n is from 0 to 3.

The amine salts of the auxin herbicides are in many cases water soluble and aqueous formulations of the amine salts are convenient to use. High concentrations of the amine salts can be prepared thereby potentially minimising the need to transport water in the formulated product while at the same time avoiding or minimising the need to use solvents with the potential disadvantages of flammability, and residue.

At the site of use the concentrate formulations can conveniently be diluted in a spray tank for soil or foliar application.

One of the significant limitations on the formulation and use of the auxin amine salts is the poor solution stability at low temperature particularly in highly concentrated solutions, for example of at least 500 g/L (based on active acid equivalent). This places limitations on the storage and handling of the auxin amine salts with the result that the loading of salt needs to be lower than would normally be stable due to the propensity to form a significant proportion of crystalline deposits at low temperature which are not always readily redissolved.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY

We have found that the solution stability of the auxins may be significantly improved allowing significantly higher loadings to be formulated by using a combination of the monomethylamine (MMA) and dimethylamine (DMA) salts of at least one of 2,4-D and dicamba in particular molar ratio of monomethylamine to dimethylamine.

Accordingly, we provide an aqueous liquid herbicide composition comprising solution of at least one of 2,4-D and dicamba in the form of the monomethylamine salt and at least one of 2,4-D and dicamba in the form of the dimethylamine salt wherein the molar ratio of monomethylamine to dimethylamine is in the range of from 1:20 to 4:6, preferably from 1:20 to 3:7, and even more preferably from 1:20 to 1:4.

In one set of embodiments the molar ratio of monomethylamine:dimethylamine comprises no lower proportion of monomethylamine salt than 1:15, more preferably 1:12 and more preferably 1:8.

In one set of preferred embodiments we provide an aqueous liquid herbicide composition comprising solution of 2,4-D in the form of the monomethylamine salt and 2,4-D in the form of the dimethylamine salt wherein the molar ratio of monomethylamine to dimethylamine is in the range of from 1:20 to 4:6, preferably from 1:20 to 3:7, and even more preferably from 1:20 to 1:4. In this set of embodiments it is preferred that the molar ratio of monomethylamine:dimethylamine comprises no lower proportion of monomethylamine salt than 1:15, more preferably 1:12 and more preferably 1:8.

In another less preferred set of embodiments we provide an aqueous liquid herbicide composition comprising a solution of dicamba in the form of the monomethylamine salt and dicamba in the form of the dimethylamine salt wherein the molar ratio of monomethylamine to dimethylamine is in the range of from 1:20 to 4:6, preferably from 1:20 to 3:7, and even more preferably from 1:20 to 1:4. In this set of embodiments it is preferred that the molar ratio of monomethylamine:dimethylamine comprises no lower proportion of monomethylamine than 1:15, more preferably 1:12 and more preferably 1:8.

In an embodiment the concentration of auxin selected from at least one of 2,4-D and dicamba (more preferably the 2,4-D) in the aqueous composition is at least 500 g/L (preferably at least 600 g/L, more preferably at least 625 g/L, still more preferably 650 g/L and still more preferably at least 700 g/L) based on herbicidal acid equivalent.

In one embodiment there is provided a solid composition for forming the aqueous liquid herbicide composition on dilution with water the solid composition comprising auxin herbicide comprising at least one of 2,4-D and dicamba in the form of the monomethylamine salt and at least one of 2,4-D and dicamba in the form of the dimethylamine salt wherein the molar ratio of monomethylamine to dimethylamine is in the range of from 1:20 to 4:6, preferably from 1:20 to 3:7, and even more preferably from 1:20 to 1:4. In this set of embodiments it is preferred that the molar ratio of monomethylamine:dimethylamine comprises no lower proportion of monomethylamine salt than 1:15, more preferably 1:12 and more preferably 1:8.

In another embodiment there is provided a process for preparing a composition described above comprising providing at least one herbicidal auxin comprising at least one of 2,4-D and dicamba and reacting the acid form of the auxin herbicide with methylamine and dimethylamine in a molar ratio of 1:20 to 4:6, preferably from 1:20 to 3:7, and even more preferably from 1:20 to 1:4. In this set of embodiments it is preferred that the molar ratio of monomethylamine:dimethylamine comprises no lower proportion of monomethylamine salt than 1:15, more preferably 1:12 and more preferably 1:8.

In another embodiment there is provided a method of preparing an aqueous liquid herbicide composition comprising dissolving an auxin monomethylamine salt and herbicidal dimethylamine salt of an auxin herbicide in an aqueous liquid to provide a composition as hereinbefore described.

Throughout the description and the claims of this specification the word "comprise" and variations of the word, such as "comprising" and "comprises" is not intended to exclude other additives, components, integers or steps.

DETAILED DESCRIPTION

While auxin herbicide salts are generally of formula:

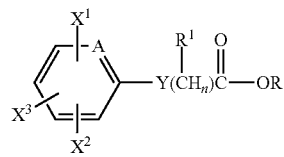

wherein
A is nitrogen or CH;
$X^1$, $X^2$ and $X^3$ are independently selected from hydrogen, halogen (preferably chloro) and methyl, preferably from hydrogen and chloro and most preferably at least two of $X^1$, $X^2$ and $X^3$ are selected from chloro and methyl;
Y is a bond, oxygen or 1,4-oxyphenoxy;
R is the monomethylamine or dimethylamine counter ion;
$R^1$ is selected from hydrogen and methyl and preferably is hydrogen; and
n is from 0 to 3;
the auxin herbicide component of the composition includes at least one selected from the group consisting of:
2,4-D (2,4-dichlorophenoxyacetic acid) and
dicamba (3,6-dichloro-o-anisic acid).

The most preferred embodiment uses 2,4-D as the auxin component.

The particularly preferred ratio of monomethylamine (MMA) to dimethylamine (DMA) is about 1:4 to 1:20.

While the composition may if desired include other herbicides including other amine salts of auxins it is preferred that the monomethylamine and dimethylamine constitute at least 80% by weight of the amine content of the composition, preferably at least 90% by weight of the amine content and most preferably at least 95% by weight of the amine content.

In a particularly preferred embodiment the concentration of auxin herbicide is at least 500 g/L (preferably at least 600 g/L, more preferably at least 625 g/L, still more preferably 650 g/L and still more preferably at least 700 g/L) based on acid herbicidal acid equivalent.

The pH of the aqueous herbicide concentrate is preferably in the range of from 6 to 10.

The composition may be prepared by mixing of the auxin amine salts in the prescribed ratio or alternatively one or both of the salts may be formed by reaction of monomethylamine and dimethylamine with the auxin. Accordingly, in one embodiment there is provided a process for preparing a auxin salt composition comprising providing at least one herbicidal auxin and reacting the acid with methylamine and dimethylamine in a molar ratio of 1:20 to 4:6, preferably from 1:20 to 3:7, and even more preferably from 1:20 to 1:4. In this set of embodiments it is preferred that the molar ratio of monomethylamine:dimethylamine comprises no lower proportion of monomethylamine than 1:15, more preferably 1:12 and more preferably 1:8.

In one embodiment there is provided a method of controlling plant growth comprising diluting a composition a concentrate composition as hereinbefore described with water and applying the diluted composition to plants or to soil in which growth of plants are to be controlled. The composition may, for example, be diluted with water to provide a concentration of auxin herbicide salt in the range of from 0.1 g/L to 150 g/L (based on acid equivalent).

The salt concentrate composition may, for example, depending on the auxin be applied at a rate of from 0.01 kg/ha to 5 kg/ha based on total acid equivalent in order to achieve control of weeds.

In some cases solvents have been used in concentrate auxin compositions such as ethylene glycol, in an attempt to limit the formation of crystalline deposits during storage of the aqueous liquid concentrate. The compositions of this invention may if desired be free of non-aqueous solvents such as ethylene glycol. Accordingly in one embodiment the herbicide composition comprising solution of auxin herbicide in the form of the monomethylamine salt and auxin herbicide in the form of the dimethylamine salt wherein the molar ratio of monomethylamine to dimethylamine is in the range of from 1:20 to 1:5 (preferably from 1:25 to 1:5 and most preferably from 1:12 to 1:3) contains no more than 5% by weight non-aqueous solvents and more preferably is essentially free of non-aqueous solvents.

In a further embodiment the composition consists essentially of:
i) auxin herbicide in the form of the monomethylamine salt and auxin herbicide in the form of the dimethylamine salt wherein the molar ratio of monomethylamine to dimethylamine is in the range of from 1:20 to 4:6, preferably from 1:20 to 3:7, and even more preferably from 1:20 to 1:4. In this set of embodiments it is preferred that the molar ratio of monomethylamine:dimethylamine comprises no lower proportion of monomethylamine salt than 1:15, more preferably 1:12 and more preferably 1:8;
ii) water;
iii) no more than 10% by weight, preferably no more than 5% and more preferably no more than 2% by weight based on the total weight of the composition of additives selected from surfactants and compatibility agents; and
iv) wherein the concentration of auxin salt herbicide in the aqueous composition is at least 500 g/L (preferably at least 600 g/L, more preferably at least 625 g/L, still more preferably 650 g/L and still more preferably at least 700 g/L) based on acid herbicidal acid equivalent.

The composition of the invention may and preferably will include a compatibility agent such as casein or EDTA which we have found to improve compatibility of the auxin amine salts and other herbicides. The amount of compatibility agent may be at least a compatibility enhancing amount. In a preferred embodiment the composition according to the invention further comprising casein in an amount of from 0.05 to 10 parts by weight casein per 100 parts by weight auxin herbicide acid equivalent. The amount of casein is preferably from 0.01 to 5% by weight of a concentrate composition and more preferably is from 0.1 to 5% by weight of the composition.

Examples of surfactants include, nonaromatic-based surfactants, e.g. those based on heterocycles, olefins, aliphatics or cycloaliphatics, for example surface-active mono- or poly-alkyl-substituted and subsequently derivatized, e.g. alkoxylated, sulfated, sulfonated or phosphated, pyridine, pyrimidine, triazine, pyrole, pyrolidine, furan, thiophene, benzoxazole, benzthiazole and triazole compounds, and/or aromatic-based surfactants, e.g. mono- or poly-alkyl-substituted and subsequently derivatized, e.g. alkoxylated, sulfated, sulfonated or phosphated, benzenes or phenols. The surfactants are generally soluble in the solvent phase and are preferably suitable for emulsifying it (together with active ingredients dissolved therein) upon dilution with water to give a spray liquor. The surfactant component when present in compositions according to the invention can, for example, comprise nonaromatic or aromatic surfactants or mixtures of nonaromatic and aromatic surfactants.

The mixed salt auxin (2,4-D and or dicamba) herbicides with the defined molar ratio of MMA:DMA exhibit an enhanced cold storage stability and reduced crystal growth at cold temperatures. The compositions also exhibit an improvement in stability in solution when diluted with water of variable quality that tends to produce precipitation in other auxins in concentrate compositions.

The invention will now be described with reference to the following examples. It is to be understood that the examples are provided by way of illustration of the invention and that they are in no way limiting to the scope of the invention.

EXAMPLES

Example 1

Figure 1:
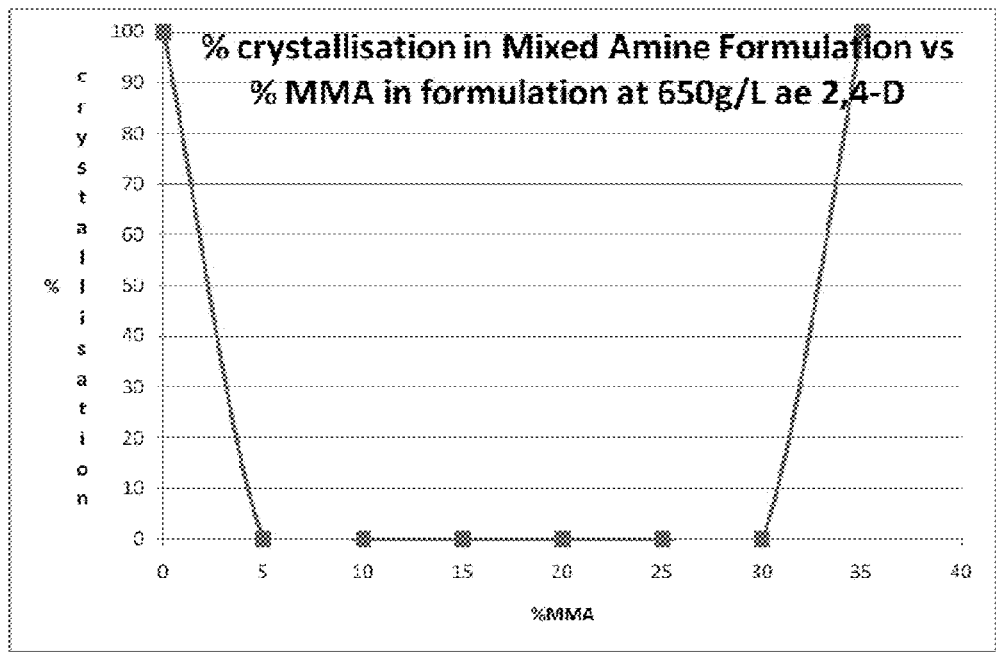
FIG. 1 is a graph showing the percent crystallisation of a 2,4-D composition of 650 g/L acid equivalent (ae) as the percentage of MMA in a MMA/DMA mixture is increased from 0 to 35%.

Five liters of a mixed amine 650 g/L 2,4-D soluble liquid was prepared. The formulation was stored at 54° C. for 14 days to evaluate its shelf life.

The composition of Example 1 was prepared by mixing the components of Table 1 in the proportions shown to provide a molar ratio of 10:90 MMA/DMA.

TABLE 1

2,4-D 650 g/L (ae) present as the DMA (90%) & MMA (10%).

| Constituent (common name) | Concentration [g/L] | Purpose in formulation |
|---|---|---|
| (a) Active constituent/s | | |
| 2,4-D technical 98% (sufficient to give 650 g/L ae 2,4-D) | 663.27 | Active |
| (b) Chemical name of other constituent/s | | |
| Dimethylamine (as 60% aqueous solution) | 198.53 | Solublising amine |
| Monomethylamine (as 40% aqueous solution) | 22.06 | Solublising amine |
| Compatibility agent | 4.00 | Compatibility agent |
| Water | to 1 liter | Solvent |

Example 2

The composition of Example 2 was prepared by mixing the components shown in Table 2 in the amounts by weight recorded to provide a 2,4-D composition comprising 2,4-D at a concentration of 700 g/L 2,4-D ae and a molar ratio of 80:20 DMA:MMA.

TABLE 2

2,4-D 700 g/L (ae) present as the DMA (80%) & MMA (20%).

| Ingredient | Weight (g) |
|---|---|
| 2,4-D Technical (98%) | 714.29 |
| MMA (40%) | 47.51 |
| DMA (60%) | 190.05 |
| Compatibility agent | 4.0 |
| Water | To 1 L |

Example 3

This example compares the storage stability at 0° C. of compositions having a range of molar proportions of monomethylamine and dimethylamine salts prepared in accordance with Example 1 at a concentration of 650 g/L ae.

The composition of Example 1 was prepared with the exception that the ratio of monomethylamine (MMA) and dimethylamine (DMA) was varied. Each example was prepared by diluting 2,4-D monomethylamine and 2,4-D dimethylamine at various ratios.

Low temperature stability testing was carried out in accordance with the Standard CIPAC Method 39.3 (1999) and the resulting percentage crystallisation is reported in Table 3.

TABLE 3

2,4-D 650 g/L (ae) with various ratios of MMA:DMA

| | % MMA | % DMA | % Crystallisation at 0 deg. C. |
|---|---|---|---|
| Formulation 3.1 | 0 | 100 | 100 |
| Formulation 3.2 | 5 | 95 | 0 |
| Formulation 3.3 | 10 | 90 | 0 |
| Formulation 3.4 | 15 | 85 | 3 |
| Formulation 3.5 | 30 | 70 | 14 |

Formulation 3.1 and Formulation 3.5 are comparative examples.

The compositions of Examples 3 and 3a comprising DMA and MMA salts of Dicamba were prepared by mixing the components identified in the following Table 4 in the amounts by weight specified.

TABLE 4

| Ingredient | Weight (g) |
|---|---|
| Example 3 DICAMBA 800 g/L (ae) present as the DMA (80%) & MMA (20%). | |
| Dicamba Technical (98%) | 853.8 |
| MMA (40%) | 62.4 |
| DMA (60%) | 249.8 |
| Compatibility agent | 4.0 |
| Water | To 1 L |
| Example 3a DICAMBA 800 g/L (ae) present as the DMA (70%) & MMA (30%) | |
| Dicamba Technical (98%) | 853.8 |
| MMA (40%) | 93.7 |
| DMA (60%) | 218.6 |
| Compatibility agent | 4.0 |
| Water | To 1 L |

Example 4

The low temperature crystallisation properties of 2,4-D MMA and DMA in mixed salt compositions were examined for compositions with active ingredient loadings of 650 ae g/L and 700 ae g/L.

Figure 2:
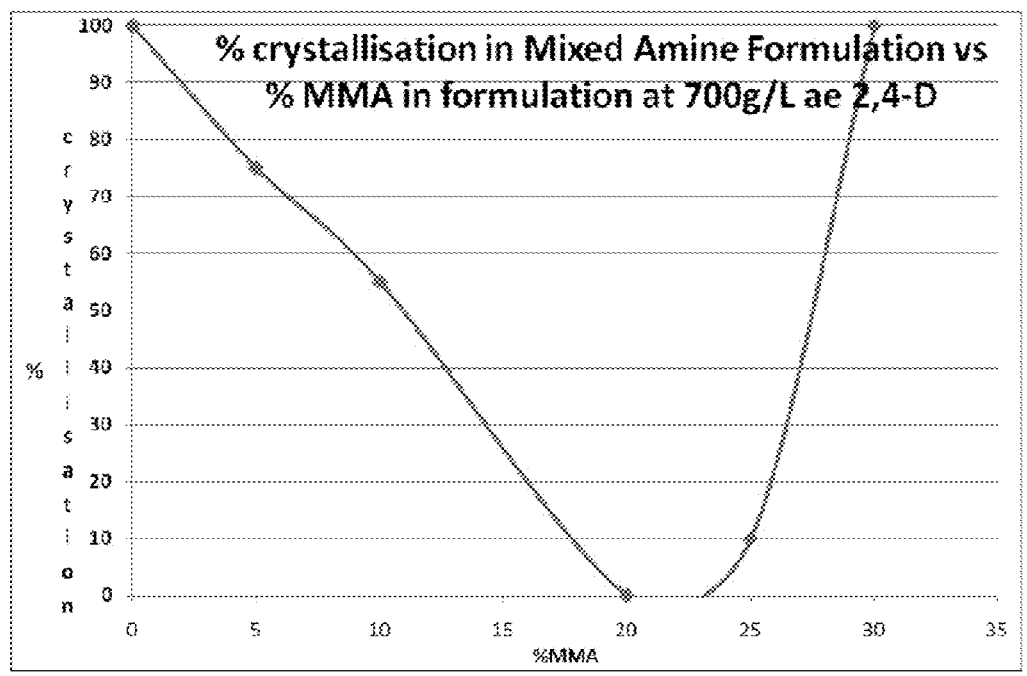
FIG. 2 is a graph showing the percent crystallisation of a 2,4-D composition of 700 g/L ae as the percentage of MMA in a MMA/DMA mixture is increased from 0 to 35%.

The results are shown in Tables 5a and 5b respectively. The crystallisation is graphically presented in FIGS. 1 and 2 respectively.

TABLE 5a 650 g/L acid equivalent 2,4-D

| Formulation | MMA | DMA | % Crystallisation at 0 deg. C. |
|---|---|---|---|
| 5a.1 | 0 | 100 | 100 |
| 5a.2 | 5 | 95 | 0 |
| 5a.3 | 10 | 90 | 0 |
| 5a.4 | 15 | 85 | 0 |
| 5a.5 | 20 | 80 | 0 |
| 5a.6 | 25 | 75 | 0 |
| 5a.7 | 30 | 70 | 0 |
| 5a.8 | 35 | 65 | 100 |

TABLE 5b 700 g/L acid equivalent 2,4-D

| Formulation | MMA | DMA | % Crystallisation at 0 deg. C. |
|---|---|---|---|
| 5b.1 | 0 | 100 | 100 |
| 5b.2 | 5 | 95 | 75 |
| 5b.3 | 10 | 90 | 55 |
| 5b.4 | 20 | 80 | 0 |
| 5b.5 | 25 | 75 | 10 |
| 5b.6 | 30 | 70 | 100 |

Example 5

Figure 3:
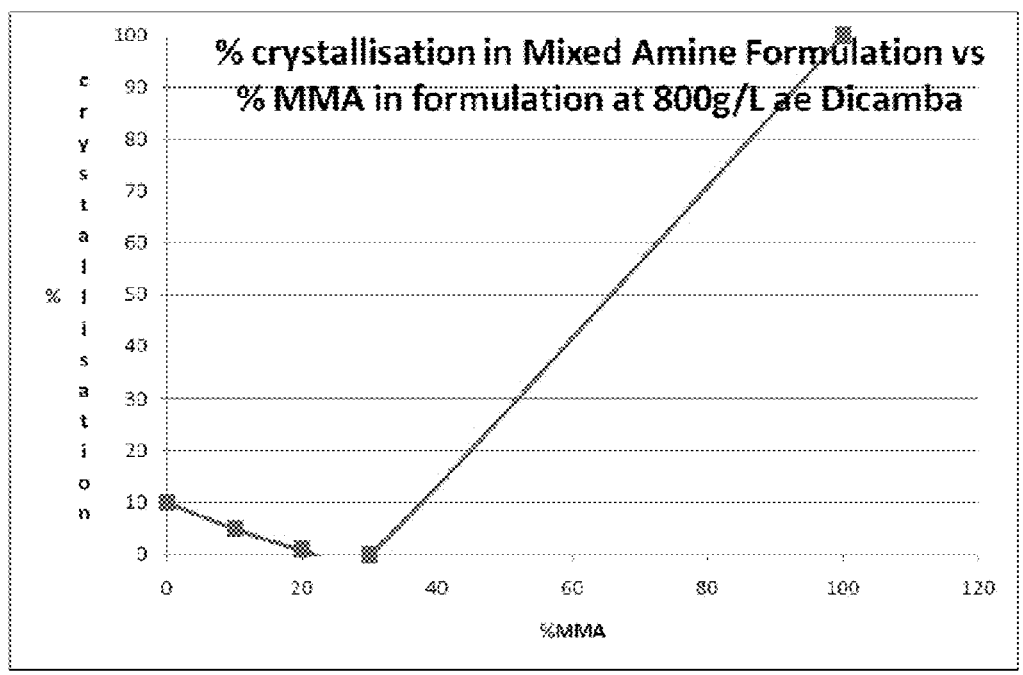
FIG. 3 is a graph showing the percent crystallisation of a Dicamba composition of 800 g/L ae as the percentage of MMA in a MMA/DMA mixture is increased from 0 to 100%.

The cold temperature crystallization in mixed salt compositions of Dicamba was determined for compositions of 700 g/L, 750 g/L and 800 g/L acid equivalent dicamba and the results are shown in Tables 6a, 6b and 6c. The percent crystallisation of DMA/MMA mixture with increasing percent MMA content for 800 g/L acid equivalent Dicamba formulations is shown on FIG. 3.

TABLE 6a

Dicamba 700 g/L ae

| Formulation | MMA | DMA | % Crystallization at 0 deg. C. |
|---|---|---|---|
| 6a.1 | 0 | 100 | 0 |
| 6a.2 | 100 | 0 | 80 |

TABLE 6b

Dicamba 750 g/L ae

| Formulation | MMA | DMA | % Crystallization at 0 deg. C. |
|---|---|---|---|
| 6b.1 | 0 | 100 | 2 |
| 6b.2 | 10 | 90 | 1 |
| 6b.3 | 20 | 80 | 0 |
| 6b.4 | 30 | 70 | 0 |

TABLE 6c

Dicamba 800 g/L ae

| Formulation | MMA | DMA | % Crystallization at 0 deg. C. |
|---|---|---|---|
| 6c.1 | 0 | 100 | 10 |
| 6c.2 | 10 | 90 | 5 |
| 6c.3 | 20 | 80 | 1 |
| 6c.4 | 30 | 70 | 0 |
| 6c.5 | 100 | 0 | 100 |

Example 6

Glass house testing of compositions of the invention were conducted in comparison with Amicide 625, a commercially available 2,4-D composition comprising 625 g/L acid equivalent of 2,4-D present as the DMA and diethanolamine salts. Formulation 5a.3—650 g ae/L 2,4-D as DMA/MMA salts in a mole ratio of 90:10 Formulation 5b.4—700 g ae/L 2,4-D as DMA/MMA in a mole ratio of salts of 80:20 Comparison—Amicide 625

Comparison Example c—500 g ae/L 2,4-D as DMA salt

The compositions were diluted and applied to distinct plots of Capeweed having 30 plants per m$^2$.

The ratio of application of 200 g/ha ae, 500 g/ha ae, 1000 g/ha ae and 2000 g/ha ae was tested for each formulation. The results are shown in Table 7. The results show that the composition provides activity in the diluted formulation equivalent to other salt formulated of 2,4-D products and yet allows higher load in the concentrate with stability against cold storage and dilution with water of variable quality.

TABLE 7

Percentage weed control of Capeweed (*Arcotheca calendula*)
50 days after application of formulations.

| | 250 gae | 500 gae | 1000 gae | 2000 gae |
|---|---|---|---|---|
| Amicide 625 | 33 | 66 | 86 | 96 |
| Formulation 5a.3 | 37 | 70 | 84 | 93 |

TABLE 7-continued

Percentage weed control of Capeweed (*Arctotheca calendula*)
50 days after application of formulations.

| | 250 gae | 500 gae | 1000 gae | 2000 gae |
|---|---|---|---|---|
| Formulation 5b.4 | 40 | 56 | 84 | 94 |
| Comparison Example c | 43 | 69 | 87 | 92 |

It is understood that various other modifications and/or alterations may be made without departing from the spirit of the present invention as outlined herein.

The invention claimed is:

1. An aqueous liquid herbicide composition comprising a solution of auxin herbicide in the form of the monomethylamine salt and auxin herbicide in the form of the dimethylamine salt, wherein the auxin herbicide is at least one of 2,4-D and dicamba, the molar ratio of monomethylamine to dimethylamine is in the range of from 1:20 to 4:6, and the concentration of auxin herbicide is at least 500 g/L based on herbicidal acid equivalent.

2. An aqueous liquid herbicide composition according to claim 1 wherein the molar ratio of monomethylamine to dimethylamine is in the range of from 1:20 to 3:7.

3. An aqueous liquid herbicide composition according to claim 1, wherein the molar ratio of monomethylamine to dimethylamine is 1:12 to 1:3.

4. An aqueous liquid herbicide composition according to claim 1, wherein the molar ratio of monomethylamine to dimethylamine is from 1:8 to 1:4.

5. An aqueous liquid herbicide composition according to claim 1, wherein the concentration of auxin herbicide is at least 600 g/L based on herbicidal acid equivalent.

6. An aqueous liquid herbicide composition according to claim 1, wherein the auxin herbicide comprises both 2,4-D and dicamba.

7. An aqueous liquid herbicide composition according to claim 1, wherein the auxin herbicide comprises 2,4-D.

8. A method of preparing an aqueous liquid herbicide composition according to claim 1, comprising dissolving an auxin herbicide in the form of the monomethylamine salt and an auxin herbicide in the form of the dimethylamine salt in an aqueous liquid, wherein the auxin herbicide is at least one of 2,4-D and dicamba, the molar ratio of monomethylamine to dimethylamine is in the range of from 1:20 to 4:6 and the concentration of auxin herbicide is at least 500 g/L based on herbicidal acid equivalent.

9. A method of preparing an aqueous liquid herbicide composition according to claim 1, comprising providing at least one auxin herbicide selected from the group consisting of 2,4-D and dicamba and reacting the at least one auxin herbicide with monomethylamine and dimethylamine in an aqueous liquid, wherein the molar ratio of monomethylamine to dimethylamine is in the range of from 1:20 to 4:6, and the concentration of auxin herbicide is at least 500 g/L based on herbicidal acid equivalent.

* * * * *